United States Patent [19]

Wegner et al.

[11] Patent Number: 4,727,081
[45] Date of Patent: Feb. 23, 1988

[54] 3,4-DIAZOLE DERIVATIVES AND PHARMACEUTICAL PREPARATIONS CONTAINING THESE COMPOUNDS

[75] Inventors: Kurt Wegner; Irene Krämer, both of Mainz; Helmut Schickaneder, Eckental; Walter Schunack, Berlin; Istvan Szelenyi, Schwaig; Kurt H. Ahrens, Nürnberg, all of Fed. Rep. of Germany

[73] Assignee: Ludwig Heumann & Co. GmbH, Nuremberg, Fed. Rep. of Germany

[21] Appl. No.: 795,992

[22] Filed: Nov. 7, 1985

[30] Foreign Application Priority Data

Nov. 9, 1984 [DE] Fed. Rep. of Germany ....... 3441086

[51] Int. Cl.$^4$ .............. A61K 31/44; C07D 417/12
[52] U.S. Cl. ............................. 514/326; 514/212; 514/230; 514/238; 514/255; 514/252; 514/316; 514/363; 514/364; 544/357; 544/364; 544/366; 546/187; 546/209; 548/138; 548/143; 548/141; 540/596; 540/597; 540/598; 540/603
[58] Field of Search ............. 548/138, 143, 141; 546/187, 209; 544/357, 364, 366; 540/596, 597, 598, 603; 514/212, 230, 238, 255, 252, 316, 326, 363, 364

[56] References Cited

FOREIGN PATENT DOCUMENTS

| 0048555 | 3/1982 | European Pat. Off. ............ 548/141 |
| 0163324 | 12/1985 | European Pat. Off. ............ 548/141 |
| 3426533 | 4/1985 | Fed. Rep. of Germany ...... 546/209 |
| 2552433 | 3/1985 | France ................................. 458/267 |
| 59-196879 | 11/1984 | Japan .................................. 546/209 |

OTHER PUBLICATIONS

March "Advanced Organic Chemistry: Reactions, Mechanisms and Structure", (McGraw-Hill) (1968), pp. 313–315, 331–332.
C.A. 102 (1985), No. 13 of Apr. 1, 1985.

Primary Examiner—Robert T. Bond

[57] ABSTRACT 3,4-Diazole derivatives corresponding to the general formula I

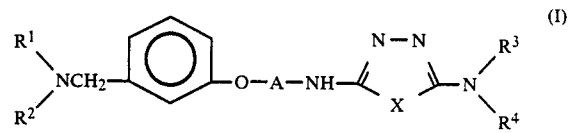

which exert a highly selective action on histamine-$H_2$ receptors are described. Processes for the preparation of these compounds and pharmaceutical preparations containing these compounds are also described.

6 Claims, No Drawings

3,4-DIAZOLE DERIVATIVES AND PHARMACEUTICAL PREPARATIONS CONTAINING THESE COMPOUNDS

This invention relates to new 3,4-diazole derivatives which have a highly selective action on histamine-$H_2$ receptors, to processes for their preparation, to pharmaceutical compositions containing these compounds, and to the use of these compounds in therapy.

Cimetidin and ranitidin have already become established as anti-ulcerative agents in therapy. Both cimetidin and ranitidin, however, have a relatively short half life, with the result that it is necessary to administer them in several daily doses of tablets with dose units of 160 to 300 mg each in a therapeutically fixed form. There therefore continues to be a need for anti-ulcerative agents which have a longer action and/or are more effective than cimetidine and ranitidine. By virtue of their specific $H_2$-antagonistic activity, the compounds according to the present invention inhibit gastric secretion which has been stimulated by histamine agonists. Ash and Shild, "Brit. J. Pharmacol. Chemother.", 27, 427 (1966) and Black et al, "Nature", 236, 385 (1972). The pharmacological activity of these compounds may be demonstrated on the perfused rat stomach by a modified method according to DE OS No. 2 734 070 or by determining the $pA_2$-values in vitro on the guinea-pig atrium (see Ariens, Molec. Pharmac., Volume 1, Academic Press, New York, 1964 ). Furthermore, the $H_2$-antagonistic action can be demonstrated on waking Heidenhain-Pouch dogs by the method of Black et al, "Nature" 236, 385 (1972) and on waking fistulated cats. The new compounds also antagonize the histamine action on the frequency of contraction of the isolated right atrium of the guinea-pig but have no influence on histamine induced contractions of isolated, smooth gastrointestinal muscle if these contractions have been produced by $H_2$-agonists. Since substances which inhibit histamine-$H_2$ receptors have an inhibitory action both on the basal gastric acid secretion and on gastric acid secretion induced by gastrin, histamine, metacholine or food, they may be used for the treatment of peptic ulcers caused by excessive gastric acid secretion as well as for the treatment of hyperacidic gastritis.

The present invention is based on the object of providing new inhibitory substances for histamine-$H_2$ receptors with improved and/or more prolonged activity. This problem is solved by the invention.

The present invention thus relates to new 3,4-diazole derivatives corresponding to the general formula I

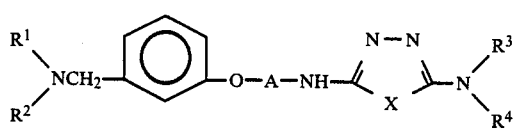

wherein $R^1$ and $R^2$, which may be identical or different, represent hydrogen or linear $C_1$-$C_{10}$-alkyl, $C_5$-$C_6$-cycloalkyl, amino, $C_1$-$C_3$-alkylamino or di-($C_1$-$C_3$-alkyl)-amino or $R^1$ and $R^2$ together with the nitrogen atom to which they are attached represent a 5- to 10-membered nitrogen-containing alicyclic or heterocylic ring optionally monosubstituted or disubstituted with a $C_1$-$C_3$-alkyl group; A represents the group $(CH_2)_n$,

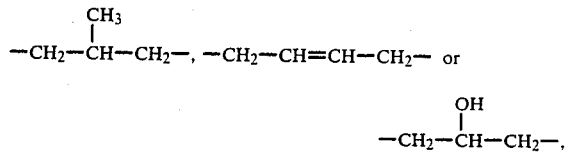

where n denotes 3 or 4; X represents an oxygen or sulphur atom; and $R^3$ and $R^4$, which may be identical or different, represent hydrogen, a linear or branched chain $C_1$-$C_6$-alkyl or $C_5$-$C_6$-cycloalkyl group or a benzyl, benzoyl or phenyl group optionally substituted by a nitro, halogen or $C_1$-$C_3$-alkyl group or $R^3$ and $R^4$ together with the nitrogen atom to which they are attached represent a 5- to 7-membered, nitrogen-containing alicyclic, heterocyclic ring, and to the physiologically acceptable salts thereof.

In the general formula I, the substituents $R^1$ and $R^2$, which may be identical or different, denote each a hydrogen atom, a linear $C_1$-$C_{10}$-alkyl group, preferably a linear $C_1$-$C_6$-alkyl group and most preferably a linear $C_1$-$C_3$-alkyl group, a $C_5$-$C_6$-cycloalkyl group, i.e. a cyclopentyl or cyclohexyl group, an amino group, a $C_1$-$C_3$-alkylamino group, e.g. a n- or i- propylamino group, an ethylamino group or a methylamino group, the methylamino group being preferred, or a di-($C_1$-$C_3$-alkyl)-amino group, preferably a diethyl- or dimethyl-amino group. Alternatively, $R^1$ and $R^2$ together with the nitrogen atom to which they are attached may form a 5- to 10- membered nitrogen-containing alicyclic, heterocyclic ring optionally mono- or disubstituted with a $C_1$-$C_3$-alkyl group. The said ring may in addition contain one or more other hetero atoms, e.g. an additional nitrogen atom or an oxygen atom or sulphur atom. Preferred examples of the 5- to 10-membered heterocyclic ring conforming to this definition are the pyrrolidine, piperidine and homopiperidine ring. Preferred examples of heterocyclic rings containing additional hetero atoms are the piperazine and the morpholine ring. In the case of monosubstitution or disubstitution on the 5- to 10-membered, nitrogen-containing alicyclic, heterocyclic ring, each of the substituents is a $C_1$-$C_3$-alkyl group, preferably a methyl group. Thus, for example, the pyrrolidine, piperidine or homopiperidine ring may be substituted with a methyl group in the 2-, 3- or 4-position or, in the case of disubstitution, in the 3,5- or 2,6-position. The following are examples of preferred substituted, nitrogen-containing 5- to 10-membered alicyclic, heterocyclic rings: the 3-methylpyrrolidine, 3-methylpiperidine, 4-methylpiperidine and 3,5-dimethylpiperidine ring, the 3-methylpyrrolidine and 3-methylpiperidine ring being particularly preferred.

The symbol A denotes one of the following groups:

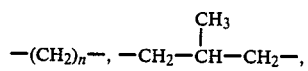

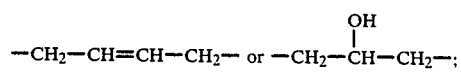

n denotes the integer 3 or 4, the value 3 being preferred. X denotes an oxygen or sulphur atom, preferably a sulphur atom. The substituents $R^3$ and $R^4$ may also be identical or different and denote hydrogen, a linear or branched $C_1$-$C_6$-alkyl group, preferably a $C_1$-$C_3$ alkyl group, e.g. an i- or n-propyl group or an ethyl or methyl group, in particular a methyl group, or a $C_5$–$C_6$-cycloalkyl group, i.e. a cyclopentyl or cyclohexyl group, or a benzyl, benzoyl or phenyl group. The benzyl benzoyl or phenyl group may be unsubstituted or it may be substituted by a nitro group, a halogen atom or a $C_1$–$C_3$-alkyl group, in particular a methyl group. $R^3$ and $R^4$ may also combine with the nitrogen atom to which they are attached to form a 5- to 7-membered, nitrogen-containing alicyclic, heterocyclic ring, the piperidine ring being preferred. Such a ring may contain an additional hetero atom, for example a nitrogen atom, an oxygen atom or a sulphur atom. Preferred examples of such a ring are the morpholine ring and the piperazine ring.

A preferred group of compounds according to the invention is characterised in that one of the substituents, $R^1$ and $R^2$, is a hydrogen atom and the other is a $C_1$–$C_3$-alkyl group, preferably a methyl group, the symbols A, X, $R^3$ and $R^4$ having the meanings defined above. Another preferred group of compounds according to the invention is characterised in that $R^1$ and $R^2$ each represents a $C_1$–$C_3$-alkyl group, in particular a methyl group, while A, X, $R^3$ and $R^4$ have the meanings defined above The invention also covers all stereoisomeric forms and hydrates of the compounds of general formula I described above.

The compounds according to the invention may be prepared by a process which is characterised in that (a) for the preparation of compounds in which $R^1$, $R^2$ and A have the meanings indicated above, $R^3$ represents hydrogen, $R^4$ represents a straight chain or branched $C^1$–$C^6$-alkyl, $C^5$–$C^6$-cycloalkyl or a benzyl, benzoyl or phenyl group optionally substituted by a nitro, halogen or $C^1$–$C^3$-alkyl group and X represents an oxygen or sulphur atom, a compound corresponding to the general formula II

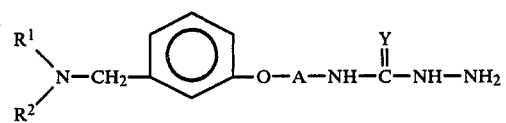

(II)

wherein $R^1$, $R^2$ and A have the meaning defined above and Y represents an oxygen or sulphur atom is reacted with an isocyanide dichloride corresponding to the general formula III

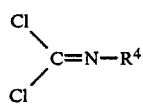

(III)

wherein $R^4$ has the meaning defined above to form a compound corresponding to the general formula I or in that (b) for the preparation of compounds in which $R^1$, $R^2$ and A have the meanings indicated above, $R^3$ and $R^4$, which may be identical or different, represent a straight chained or branched $C_1$–$C_6$-alkyl or $C_5$–$C_6$cycloalkyl or a benzyl, benzoyl or phenyl group optionally substituted by a nitro, halogen or $C_1$–$C_3$-alkyl group or $R_3$ and $R_4$ together with the nitrogen atom to which they are attached represent a 5- to 7-membered, nitrogen-containing alicyclic, heterocyclic ring and X represents a sulphur atom, a compound corresponding to the general formula IV

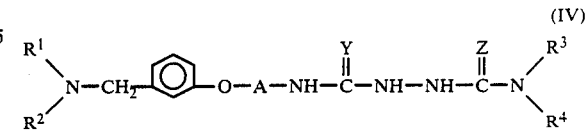

(IV)

wherein $R^1$, $R^2$, 3, $R^4$ and A have the meanings defined above and Y and Z represent each a sulphur atom, is cyclised with the aid of an oxidizing agent to form a compound corresponding to the general formula I, or in that (c) for the preparation of compounds in which $R^1$, $R^2$ and A have the meanings indicated above, $R^3$ and $R^4$, which may be identical or different, represent straight chained or branched $C_1$–$C_6$-alkyl, $C_5$–$C_6$-cycloalkyl or a benzyl, benzoyl or phenyl group optionally substituted by a nitro, halogen or $C_1$–$C_3$-alkyl group or $R^3$ and $R^4$ together with the nitrogen atom to which they are attached represent a 5- to 7-membered, nitrogen-containing, alicyclic, heterocyclic ring, and X represents a sulphur atom, a compound corresponding to the general formula IV

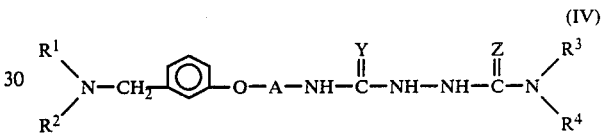

(IV)

wherein $R^1$, $R^2$, $R^3$, $R^4$ and A have the meanings defined above and Y and Z are either identical and represent each a sulphur atom or are different from one another and represent either an oxygen atom or a sulphur atom is cyclised with phosphorus oxychloride to form a compound corresponding to the general formula I or in that (d) for the preparation of compounds in which $R^1$, $R^2$ and A have the meanings indicated above, $R^3$ and $R^4$, which may be identical or different, represent straight chained or branched $C_1$–$C_6$-alkyl, $C_5$–$C_6$-cycloalkyl a benzyl, benzoyl or phenyl group optionally substituted by a nitro, halogen or $C_1$–$C_3$-alkyl group, or $R^3$ and $R^4$ together with the nitrogen atom to which they are attached represent a 5- to 7-membered, nitrogen-containing, alicyclic, heterocyclic ring, and X represents an oxygen atom, a compound corresponding to the general formula IV

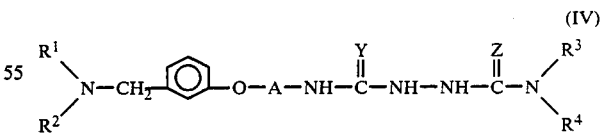

(IV)

wherein $R^1$, $R^2$, $R^3$, $R^4$, and A have the meanings defined above and Y and Z represent each an oxygen atom, is cyclodehydrated with phosphorus oxychloride to form a compound corresponding to the general formula I, or in that (e) for the preparation of compounds in which $R^1$, $R^2$ and A have the meanings indicated above, $R^3$ and $R^4$ each denote hydrogen and X represents an oxygen or sulphur atom, a compound corresponding to the general formula V

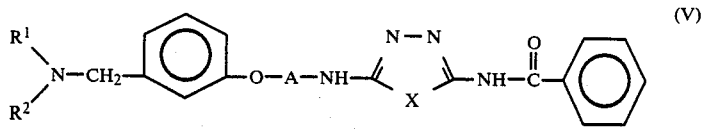 (V)

wherein $R^1$, $R^2$ and A have the meanings defined above is hydrolysed to a compound corresponding to the general formula I or in that (f) for the preparation of compounds in which $R^1$, $R^2$, $R^3$, $R^4$ and A have the meanings indicated above and X represents a sulphur atom, an amine corresponding to the general formula VI

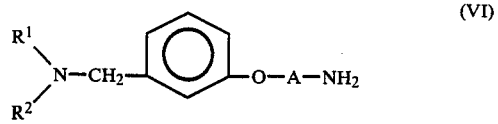 (VI)

wherein $R^1$, $R^2$ and A have the meanings defined above is reacted with a 1,3,4-thiadiazole-2-amine corresponding to the general formula VII

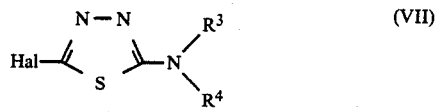 (VII)

wherein Hal represents a halogen atom and $R^3$ and $R^4$ have the meanings defined above, to form a compound corresponding to the general formula I, or in that (g) for the preparation of compounds in which $R^1$, $R^2$, 4 and A have the meanings defined above and $R^3$, $R^4$ and A have the meanings defined above and X represents a sulphur atom, a compound corresponding to the general formula (VIII)

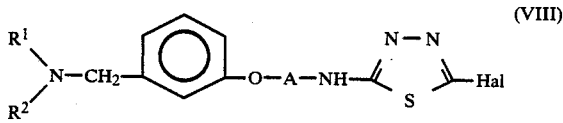 (VIII)

wherein $R^1$, $R^2$ and A have the meanings defined above and Hal represents a halogen atom is reacted with an amine corresponding to the general formula IX

 (IX)

wherein $R^3$ and $R^4$ have the meanings defined above, to form a compound corresponding to the general formula I and in that the compound obtained in stages (a) to (g) is optionally converted into a physiologically harmless salt thereof.

The method of synthesis according to variation (a) is carried out in known manner. The reaction is advantageously carried out in a solvent, preferably in an aprotic solvent such as, for example, dioxane or tetrahydrofuran. The reaction is preferably carried out at an elevated temperature, for example at the reflux temperature of the solvent used, and generally takes from 1 to 3 hours.

Isolation, working up and purification of the reaction product are also carried out in known manner, for example by preparative layer chromatography.

The method of synthesis according to variation (b) is also carried out in known manner and again preferably using a solvent, e.g. an aprotic solvent as defined above. The oxidizing agent used is preferably hydrogen peroxide. Working up and isolation of the product are carried out in known manner, for example by preparative thick layer chromatography.

The same applies to variations (c) to (g), which are also carried out in known manner.

Preparation of the starting products described under (a) to (g) may in principle be carried out by known methods of synthesis for 1,3,4-oxa-(thia)diazole-2,5-diamines (see 1. W. R. Sherman in "Heterocyclic Compounds", Vol.7, 541–626 (published by R. C. Elderfield, Wiley, New York, 1961),
2. J. Sandström in "Advances in Heterocyclic Chemistry", Vol.9, 165–209 (published by A. R. Katritzky and A.J. Boulton, Academic Press, New York (1968), Recent advances in the chemistry of 1,3,4-thiadiazoles,
3. A. Hetzheim and K. Möckel in "Advances in Heterocyclic Chemistry", Vol.7 (published by A. R. Katritzky and A. J.Boulton, Academic Press, New York, (1968), and
4. G. Werber et al, J. Heterocycl. Chem. 14, 823 (1977)).

It has been found that these starting products also manifest a certain $H_2$ antagonistic activity and could therefore possibly also be used for therapeutic purposes.

The invention covers not only the stereoisomeric compounds and hydrates of the substances corresponding to the general formula I but also the physiologically acceptable salts of these compounds. The said salts may be formed, for example, with mineral acids such as hydrochloric, hydrobromic or hydriodic acid, phosphoric acid, metaphosphoric acid, nitric acid or sulphuric acid or with organic acids such as formic acid, acetic acid, propionic acid, phenylacetic acid, tartaric acid, citric acid, fumaric acid, methanesulphonic acid, etc.

As already mentioned above, the compounds according to the invention constitute effective $H_2$-antagonists which are superior to reputable compounds having a similar action, such as CIMETIDIN and RANITIDIN.

The invention therefore also relates to medicaments, in particular for the treatment of gastrointestinal diseases, which is characterised in that they contain, as active ingredient, at least one of the above described compounds together with an inert, pharmaceutically acceptable carrier or diluent.

The compounds according to the invention may be administered in any suitable formulation. The invention therefore also covers medicaments containing at least one compound according to the invention for use in human or veterinary medicine. Such medicaments may be prepared by conventional methods, using one or more pharmaceutical carriers or diluents.

The compounds according to the invention may therefore be formulated for oral, buccal, local, parenteral or rectal administration, oral administration being preferred.

For oral administration, the medicament may be formulated, for example, as tablets, capsules, powders, solutions, syrups or suspensions prepared by the conventional methods, using acceptable diluents.

For buccal administration, the medicament may be made up into tablets or sachets formulated in the conventional manner.

For parenteral administration, the compounds according to the invention may be formulated for bolus injection or continuous infusion. Formulations for injection may be made up as ampoules of unit doses or prepared in multiple dose containers with added preservatives.

The pharmaceutical preparations may assume the form of suspensions, solutions or emulsions in oily or aqueous carriers and may contain formulating auxiliaries such as suspending and/or dispersing agents or stabilizers.

Alternatively, the active ingredient may be provided in powder form to be reconstituted before use with a suitable carrier such as sterile, pyrogen-free water.

The compounds according to the invention may also be formulated for rectal administration, for example as suppositories or retention enemas containing, for example, conventional suppository excipients such as cocoa butter or other glycerides.

For local application, the compounds according to the invention may be made up into conventional forms of ointments, creams, gels, lotions, powders or sprays.

For oral administration, a suitable daily dose of compounds according to the invention is from 1 to 4 doses adding up to a total of from 5 mg to 1 g per day, preferably from 5 to 250 mg per day, depending on the patient's condition. In individual cases, it may be necessary to deviate from these quantities, depending on the individual response to the active substance or its formulation and the point in time or time interval at which the medicament is administered. Thus in some cases, for example, it may be sufficient to administer less than the minimum quantity indicated above whereas in other cases it may be necessary to exceed the maximum quantity.

The invention will now be illustrated in the Examples. Examples 1 to 4 describe the preparation of starting compounds corresponding to the general formula II. Examples 5 to 28 describe the preparation of starting compounds corresponding to the general formula IV. Examples 29 to 70 describe the preparation of compounds according to the invention corresponding to the general formula I.

EXAMPLE 1

N-[3-[3-(1-Piperidinylmethyl)phenoxy]propyl]hydrazine carboxamide 6.3 g (40 mmol) of phenyl chloroformate are slowly added dropwise at room temperature to a solution of 10.0 g (40 mmol) of 3-[3-(1-piperidinylmethyl)phenoxy]-1-propanamine in 200 ml of absolute ether. A solution of 1.6 g (40 mmol) of sodium hydroxide in 16 ml of water is added dropwise simultaneously with the second half of the ester. The reaction mixture is stirred for one hour and the phases are then separated. The ether phase is washed, dehydrated over sodium sulphate and concentrated by evaporation. The oily residue is taken up with 250 ml of an ethanol/ether mixture (1:1) and gassed with anhydrous hydrogen chloride at 0° C. until the product has completely precipitated.

Yield: 13 g of N-[3-[3-(1-piperidinylmethyl)phenoxy]propyl]carbamic acid phenyl ester hydrochloride; melting point: 144° C.

$C_{22}H_{28}N_2O_3 \cdot HCl$ (404.9) Calculated: C 65.3; H 7.22; N 6.92. Found: C 65.2; H 6.97; N 7.09.

13 g (32 mmol) of the ester prepared as described above are dissolved in 100 ml of ethanol with the addition of 4.5 ml (32 mmol) of triethylamine, 15 g (0.3 mol) of hydrazine hydrate are added, and the reaction mixture is heated under reflux for 3 hours. The mixture is then concentrated by evaporation under vacuum, and excess hydrazine hydrate is to a large extent distilled off. The oily residue is purified by column chromatography (silica gel; methylene chloride saturated with ammonia).

Yield: 7 g of colourless oil (72% of theoretical)
$C_{16}H_{26}N_4O_2$ (306.4)
1H-NMR (CDCl$_3$; TMS): $\partial$=1.3–1.7 (m)(—(CH$_2$)$_3$-) 6H; 1.97 (m) (CH$_2$) 2H; 2.2–2.5 (m) (-(CH$_2$)$_2$-) 4H; 3.1–3.7 (m) (N-CH$_2$, NH$_2$ (replaceable by D$_2$O)) 4H; 3.37 (s) (CH$_2$) 2H; 4.00 (t) (O—CH$_2$) 2H; 6.34 (t) (NH) (replaceable by D$_2$O))1H; 6.6–7.3 (m) (aromatic-H, NH (replaceable by D$_2$O)) 5 H.

EXAMPLE 2

N-[2-Methyl-3-[3-(1-piperidinylmethyl)phenoxy]propyl]hydrazine carboxamide 2.2 g (8 mmol) of 2-methyl-3-[3-(1-piperidinylmethyl)phenoxy]-1-propanamine in 20 ml of ethanol are stirred together with 1.9 g (8 mmol) of diphenylcarbonate at room temperature for 12 hours. 4 g of hydrazine hydrate is then added to the solution and the reaction mixture is heated under reflux for one hour. Isolation of the product is carried out as described in Example 1.

Yield: 1.1 g of colourless oil (43% of theoretical)
$C_{17}H_{27}N_4O_2$ (319.4) 1H-NMR (CDCl$_3$; TMS): $\partial$=1.33 (d) (CH$_3$) 3H; 1.3–1.7 (m) (—(CH$_2$)$_3$-) 6H; 1.9–2.5 (m) (-(CH$_2$)$_2$-, CH) 5H, 3.1–3.7 (m) (N-CH$_2$,NH$_2$ (replaceable by D$_2$O)) 4H; 3.40 (s) (CH$_2$) 2H; 3.86 (d) (O—CH$_2$) 2H; 6.40 (t) (NH (replaceable by D$_2$O)) 1H; 6.6–7.3 (m) (aromatic-H, NH (replaceable by D$_2$O)) 5H.

EXAMPLE 3

N-[3-[3-(1-Piperidinylmethyl)phenoxy]propyl]hydrazine carbothioamide 49.7 g (0.2 mol) of 3-[3-(1-piperidinylmethyl)phenoxy]1-propanamine in 200 ml of ethanol are added dropwise to a mixture of 200 ml of ethanol and 200 ml of carbon disulphide with vigorous stirring and the mixture continues to be stirred overnight. After removal of the carbon disulphide by evaporation, 30 g (0.21 mol) of methyl iodide are added to the ethanolic suspension which is then stirred until completely dissolved. The solution is concentrated by evaporation to about 200 ml, 50 ml of hydrazine hydrate are added, and the reaction mixture is left to stand at room temperature for 48 hours. The crystallisate obtained is separated by suction filtration and washed with cold ethanol.

Yield: 51 g (79% of theoretical)
$C_{16}H_{26}N_4OS$ (322.5); melting point: 116° C. (ethanol)
Calculated: C 59.6; H 8.13; N 17.4, Found: C 59.4; H 8.04; N 17.3.

EXAMPLE 4

N-[2-Hydroxy-3-[3-(1-piperidinylmethyl)-phenoxy]-propyl]hydrazine carbothioamide 3.97 g (15 mmol) of 1-amino-3-[3-(1-piperidinylmethyl)phenoxy]-2-propanol are reacted by a method analogous to that of Example 3. After concentration of the reaction solution by evaporation, the oily residue is digested several times with water, centrifuged, dried and crystallised by the addition of ether.

Yield: 2.5 g (67% of theoretical)

$C_{16}H_{26}N_4O_2S$ (338.5); Melting point: 91°–93° C. (acetonitrile/ether) Calculated: C 56.8; H 7.74; N 16.6. Found: C 56.6; H 7.65; N 16.6.

EXAMPLE 5

N-Methyl-N'-[3-[3-(1-piperidinylmethyl)phenoxy]-propyl]1,2-hydrazine dicarbothioamide 1.62 g (5 mmol) of N-[3-[3-(1-piperidinylmethyl)phenoxy]propyl]hydrazine carbothioamide are dissolved in 30 ml of THF, 0.44 g (6 mmol) of methyl isothiocyanate are added, and the reaction mixture is left to stand overnight at room temperature. Ether is added to complete precipitation and the precipitate formed is suction filtered, washed with ether and recrystallised from ethanol. The analytical values are summarized in Table I.

EXAMPLE 6

N-Ethyl-N'-[3-[3-(1-piperidinylmethyl)phenoxy]-propyl]1,2-hydrazine dicarbothioamide The above compound is prepared by a method analogous to that of Example 5 from N-[3-[3-(1-piperidinylmethyl)phenoxy]propyl]-hydrazine carbothioamide and ethylisothiocyanate. The analytical values are summarized in Table I.

EXAMPLE 7

N-Cyclohexyl-N'-[3-[3-(1-piperidinylmethyl)phenoxy]-propyl]1,2-hydrazine dicarbothioamide The compound is prepared by a method analogous to that of Example 5 from N-[3-[3-(1-piperidinylmethyl)-phenoxy]propyl]hydrazine carbothioamide and cyclohexylisothiocyanate. The analytical values are summarized in Table I.

EXAMPLE 8

N-Benzoyl-N'-[3-[3-(1-piperidinylmethyl)phenoxy]-propyl]1,2-hydrazine dicarbothioamide The compound is prepared by a method analogous to that of Example 5 from N-[3-[3-(1-piperidinylmethyl)-phenoxy]propyl] hydrazine carbothioamide and benzoyl isothiocyanate. The analytical values are summarized in Table I.

EXAMPLE 9

N-Methyl-2-[[3-[3-(1-piperidinylmethyl)phenoxy]-propyl]aminothioxomethyl]-hydrazine carboxamide 1.62 g (5 mmol) of N-[3-[3-(1-piperidinylmethyl)-phenoxy]propyl]hydrazine carbothioamide are dissolved in 30 ml of THF, 0.40 g (6 mmol) of methylisocyanate are added and the reaction mixture is left to stand overnight at room temperature. Ether is added to complete the precipitation, and the precipitate is suction filtered, washed with ether and recrystallised from ethanol. The analytical values are summarized in Table I.

EXAMPLE 10

N-Ethyl-2-[[3-[3-(1-piperidinylmethyl)phenoxy]propyl]aminothioxomethyl]-hydrazine carboxamide The compound is prepared by a method analogous to that of Example 9 from N-[3-[3-(1-piperidinylmethyl)-phenoxy]propyl]-hydrazine carbothioamide and ethyl isocyanate. The analytical values are summarized in Table I.

EXAMPLE 11

N-Isopropyl-2-[[3-[3-(1-piperidinylmethyl)phenoxy]-propyl]aminothioxomethyl]hydrazine carboxamide The compound is prepared by a method analogous to that of Example 9 from N-[3-[3-(1-piperidinylmethyl)-phenoxy]propyl]-hydrazine carbothioamide and isopropyl isocyanate. The analytical values are summarized in Table I.

EXAMPLE 12

N-Butyl-2-[[3-[3-(1-piperidinylmethyl) phenoxy]propyl]aminothioxomethyl]-hydrazine carboxamide The compound is prepared by a method analogous to that of Example 9 from N-[3-[3-(1-piperidinylmethyl)-phenoxy]propyl]-hydrazine carbothioamide and n-butylisocyanate. The analytical values are summarized in Table I.

EXAMPLE 13

N-Cyclohexyl-2-[[3-[3-(1-piperidinylmethyl)phenoxy]-propyl]aminothioxomethyl]-hydrazine carboxamide The compound is prepared by a method analogous to that of Example 9 from N-[3-[3-(1-piperidinylmethyl)-phenoxy]propyl]-hydrazine carbothioamide and cyclohexyl isocyanate. The analytical values are summarized in Table I.

EXAMPLE 14

N-Benzyl-2-[[3-[3-(1-piperidinylmethyl)phenoxy]-propyl]aminothioxomethyl]-hydrazine carboxamide The compound is prepared by a method analogous to that of Example 9 from N-[3-[3-(1-piperidinylmethyl)-phenoxy]propyl]-hydrazine carbothioamide and benzyl isocyanate. The analytical values are summarized in Table I.

EXAMPLE 15

N-Phenyl 2-[[3-[3-(1-piperidinylmethyl)phenoxy]propyl]aminothioxomethyl]-hydrazine carboxamide The compound is prepared by a method analogous to that of Example 9 from N-[3-[3-(1-piperidinylmethyl) phenoxy]propyl]-hydrazine carbothioamide and phenyl isocyanate. The analytical values are summarized in Table I.

EXAMPLE 16

N-4-Chlorophenyl-2-[[3-[3-(1-piperidinylmethyl)-phenoxy]propyl]aminothioxomethyl]-hydrazine carboxamide The compound is prepared by a method analogous to that of Example 9 from N-[3-[3-(1-piperidinylmethyl)- phenoxy]propyl]-hydrazine carbothioamide and 4-chlorophenyl isocyanate. The analytical values are summarized in Table I.

EXAMPLE 17

2-(Methylaminothioxomethyl)-N-[3-[3-(1-piperidinylmethyl)phenoxy]-propyl]-hydrazine carboxamide 0.5 g (6.6 mmol) of methylisothiocyanate are added to 1.0 g (3.3 mmol) of N-[3-[3-(1-piperidinylmethyl)phenoxy]propyl]-hydrazine carboxamide in 20 ml of THF and the mixture is stirred at room temperature for 12 hours. The precipitate obtained is filtered off and recrystallised from ethanol. The analytical values are summarized in Table I.

EXAMPLE 18

2-(Ethylaminothioxomethyl)-N-[3-[3-(1-piperidinylmethyl)phenoxy]propyl]-hydrazine carboxamide The compound is prepared by a method analogous to that of Example 17 from N-[3-[3-(1-piperidinylmethyl)phenoxy]propyl]-hydrazine carboxamide and ethyl isothiocyanate. The analytical values are summarized in Table I.

EXAMPLE 19

2-(Cyclohexylaminothioxomethyl)-N-[3-[3-(1-piperidinylmethyl)phenoxy]propyl]-hydrazine carboxamide The compound is prepared by a method analogous to that of Example 17 from N-[3-[3-(1-piperidinylmethyl)phenoxy]propyl]-hydrazine carboxamide and cyclohexyl isothiocyanate. The analytical values are summarized in Table I.

EXAMPLE 20

N-Methyl-N'-[3-[3-(1-piperidinylmethyl)phenoxy]propyl]1,2-hydrazine dicarboxamide 0.8 ml (13 mmol) of methylisocyanate are added to 2.0 g (6.6 mmol) of N-[3-[3-(1-piperidinylmethyl)phenoxy]-propyl]-hydrazine carboxamide in 20 ml of THF and the reaction mixture is stirred at room temperature for one hour. The precipitate is filtered off and recrystallised from methanol. The analytical values are summarized in Table I.

EXAMPLE 21

N-Ethyl-N'-[3-[3-(1-piperidinuylmethyl)phenoxy]propyl]1,2-hydrazine dicarboxamide The compound is prepared by a method analogous to that of Example 20 from N-[3-[3-(1-piperidinylmethyl)phenoxy]propyl]-hydrazine carboxamide and ethyl isocyanate. The analytical values are summarized in Table I.

EXAMPLE 22

N-Isopropyl-N'-[3-[3-(1-piperidinylmethyl)phenoxy]propyl]1,2-hydrazine dicarboxamide The compound is prepared by a method analogous to that of Example 20 from N-[3-[3-(1-piperidinylmethyl)phenoxy]propyl]-hydrazine carboxamide and isopropyl isocyanate. The analytical values are summarized in Table I.

EXAMPLE 23

N-Cyclohexyl-N'-[3-[3-(1-piperidinylmethyl)phenoxy]propyl]1,2-hydrazine dicarboxamide The compound is prepared by a method analogous to that of Example 20 from N-[3-[3-(1-piperidinylmethyl)phenoxy]propyl]-hydrazine carboxamide and cyclohexyl isocyanate. The analytical values are summarized in Table I.

EXAMPLE 24

N-Benzyl-N'-[3-[3-(1-piperidinylmethyl)-phenoxy]propyl]1,2-hydrazine dicarboxamide The compound is prepared by a method analogous to that of Example 20 from N-[3-[3-(1-piperidinylmethyl)phenoxy]propyl]-hydrazine carboxamide and benzyl isocyanate. The analytical values are summarized in Table I.

EXAMPLE 25

N-Phenyl-N'-[3-[3-(1-piperidinylmethyl)phenoxy]propyl]-1,2hydrazine dicarboxamide The compound is prepared by a method analogous to that of Example 20 from N-[3-[3-(1-piperidinylmethyl)phenoxy]propyl]-hydrazine carboxamide and phenyl isocyanate. The analytical values are summarized in Table I.

EXAMPLE 26

N-4-Chlorophenyl-N'-[3-[3-(1-piperidinylmethyl)-phenoxy]propyl]-1,2-hydrazine dicarboxamide The compound is prepared by a method analogous to that of Example 20 from N-[3-[3-(1-piperidinylmethyl)phenoxy]propyl]-hydrazine carboxamide and 4-chlorophenyl isocyanate. The analytical values are summarized in Table I.

TABLE I

Characteristics of the starting compounds of Examples 5 to 26 corresponding to the general formula

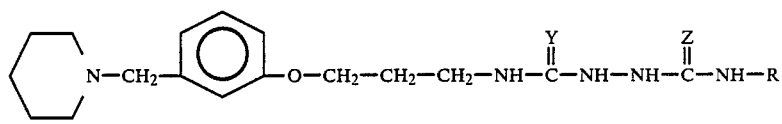

| Example | R | Y Z | Overall formula Molecular weight | Analysis: Calculated/Found | | | Melting point °C. | Yield % of theoretical |
|---|---|---|---|---|---|---|---|---|
| | | | | C | H | N | | |
| 5 | $CH_3$ | S S | $C_{18}H_{29}N_5OS_2$ 395.6 | 54.7 54.7 | 7.39 7.23 | 17.7 17.9 | 154–6 | 78 |
| 6 | $C_2H_5$ | S S | $C_{19}H_{31}N_5OS_2$ 409.6 | 55.7 55.6 | 7.63 7.58 | 17.1 17.0 | 145–6 | 50 |

TABLE I-continued
Characteristics of the starting compounds of Examples 5 to 26 corresponding to the general formula

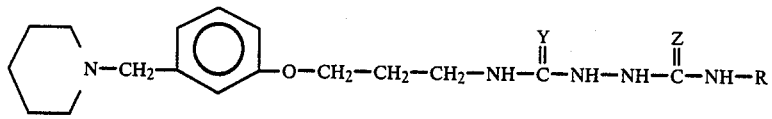

| Example | R | Y Z | Overall formula Molecular weight | Analysis: Calculated/Found | | | Melting point °C. | Yield % of theoretical |
|---|---|---|---|---|---|---|---|---|
| | | | | C | H | N | | |
| 7 | c-C$_6$H$_{11}$ | S S | C$_{23}$H$_{37}$N$_5$OS$_2$ 463.7 | 59.6 59.4 | 8.04 8.08 | 15.1 15.2 | 171-2 | 43 |
| 8 | COC$_6$H$_5$ | S S | C$_{24}$H$_{31}$N$_5$O$_2$S$_2$ × HCl 522.1 | 55.2 55.3 | 6.18 6.26 | 13.4 13.7 | 175-7 | 79 |
| 9 | CH$_3$ | S O | C$_{18}$H$_{29}$N$_5$O$_2$S 379.5 | 57.0 56.8 | 7.70 7.73 | 18.5 18.2 | 187-8 | 88 |
| 10 | C$_2$H$_5$ | S O | C$_{19}$H$_{31}$N$_5$O$_2$S 393.6 | 58.0 58.1 | 7.94 7.95 | 17.8 17.9 | 180-1 | 84 |
| 11 | CH(CH$_3$)$_2$ | S O | C$_{20}$H$_{33}$N$_5$O$_2$S 407.6 | 58.9 58.8 | 8.16 8.06 | 17.2 16.9 | 205-6 | 84 |
| 12 | C$_4$H$_9$ | S O | C$_{21}$H$_{35}$N$_5$O$_2$S 421.6 | 59.8 59.8 | 8.37 8.25 | 16.6 16.3 | 192-3 | 92 |
| 13 | c-C$_6$H$_{11}$ | S O | C$_{23}$H$_{37}$N$_5$O$_2$S 447.7 | 61.7 61.3 | 8.33 8.19 | 15.6 15.6 | 208-9 | 82 |
| 14 | CH$_2$—C$_6$H$_5$ | S O | C$_{24}$H$_{33}$N$_5$O$_2$S 455.6 | 63.3 63.3 | 7.30 7.34 | 15.4 15.7 | 181-2 | 94 |
| 15 | C$_6$H$_5$ | S O | C$_{23}$H$_{31}$N$_5$O$_2$S 441.6 | 62.6 62.3 | 7.08 7.01 | 15.9 15.6 | 176-7 | 64 |
| 16 | 4Cl—C$_6$H$_4$ | S O | C$_{23}$H$_{30}$ClN$_5$O$_2$S 476.0 | 58.0 57.9 | 6.35 6.38 | 14.7 14.9 | 163-8 decomposition | 59 |
| 17 | CH$_3$ | O S | C$_{18}$H$_{29}$N$_5$O$_2$S 379.5 | 57.0 56.9 | 7.70 7.54 | 18.5 18.3 | 196 | 60 |
| 18 | C$_2$H$_5$ | O S | C$_{19}$H$_{31}$N$_5$O$_2$S 393.6 | 58.0 58.5 | 7.94 8.24 | 17.8 17.8 | 186 | 56 |
| 19 | c-C$_6$H$_{11}$ | O S | C$_{23}$H$_{37}$N$_5$O$_2$S 447.7 | 61.7 61.5 | 8.33 8.59 | 15.6 15.5 | 191 | 50 |
| 20 | CH$_3$ | O O | C$_{18}$H$_{29}$N$_5$O$_3$ 363.5 | 59.5 59.4 | 8.04 7.81 | 19.3 19.3 | 233 decomposition | 67 |
| 21 | C$_2$H$_5$ | O O | C$_{19}$H$_{31}$N$_5$O$_3$ 377.5 | 60.5 60.2 | 8.28 8.23 | 18.6 18.3 | 233 | 69 |
| 22 | CH(CH$_3$)$_2$ | O O | C$_{20}$H$_{33}$N$_5$O$_3$ 391.5 | 61.4 61.3 | 8.50 8.48 | 17.9 17.7 | 204 decomposition | 67 |
| 23 | c-C$_6$H$_{11}$ | O O | C$_{23}$H$_{37}$N$_5$O$_3$ 431.6 | 64.0 63.9 | 8.64 8.54 | 16.2 16.2 | 199 | 50 |
| 24 | CH$_2$C$_6$H$_5$ | O O | C$_{24}$H$_{33}$N$_5$O$_3$ 439.6 | 65.6 65.6 | 7.57 7.40 | 15.9 15.9 | 211 | 70 |
| 25 | C$_6$H$_5$ | O O | C$_{23}$H$_{31}$N$_5$O$_3$ 425.5 | 64.9 65.0 | 7.34 7.31 | 16.5 16.6 | 206 decomposition | 60 |
| 26 | 4-Cl—C$_6$H$_4$ | O O | C$_{23}$H$_{30}$ClN$_5$O$_3$ 460.0 | 60.1 60.2 | 6.57 6.47 | 15.2 15.0 | 203 | 60 |

EXAMPLE 27

N,N-Dimethyl-N'-[3-[3-(1-piperidinylmethyl)phenoxy]-propyl]-1,2-hydrazine dicarboxamide 0.6 ml (4 mmol) of triethylamine and 0.4 ml (4 mmol) of N,N-dimethyl-carbamide chloride are added to 1.2 g (4 mmol) of N-[3-[3-(1-piperidinylmethyl)phenoxy]-propyl]hydrazine carboxamide in 20 ml of ether and the reaction mixture is stirred for 12 hours. Solid triethylammonium chloride is filtered off and the filtrate is concentrated by evaporation under vacuum.

Yield: 1.2 g of amorphous solid (80% of theoretical) C$_{19}$H$_{31}$N$_5$O$_3$ (377.5) 1H—NMR (CDCl$_3$; TMS): $\delta$=1.3-1.7 (m) (—(CH$_2$)$_3$—) 6H; 1.90 (m) (CH$_2$) 2H; 2.2-2.5 (m) (—(CH$_2$)$_2$—) 4H; 2.87 (s) ((CH$_3$)$_2$ 6H; 3.1-3.7 (m) (N-CH$_2$, NH (replaceable by D$_2$O )) 3H; 3.57 (s) (CH$_2$) 2H; 3.97 (t) (O-CH$_2$) 2H; 6.27 (t) (NH(replaceable by D$_2$O)) 1 H; 6.6-7.3 (m) (aromatic-H) 4H; 7.57 (s) (NH (replaceable by D$_2$O)) 1H.

EXAMPLE 28

N,N-Dimethyl-2[[3-[3-(1-piperidinylmethyl)phenoxy]-propyl]aminothioxymethyl]-hydrazine carboxamide 1 ml of triethylamine and 0.6 g (6 mmol) of N,N-dimethyl-carbamide chloride are added to 1.62 g (5 mmol) of N-[3-[3-(1-piperidinylmethyl)phenoxy]-propyl]hydrazine carbothioamide in 30 ml of THF and the reaction mixture is heated under reflux for 3 hours. Solid triethylammonium chloride is filtered off, the filtrate is concentrated by evaporation and the oily residue is crystallised by the addition of ether.

Yield: 1.5 g (76% of theoretical); melting point: 91°-94° C. (ethanol/water)

C$_{19}$H$_{31}$N$_5$O$_2$S (393.6)

Calculated: C 58.0; H 7.94; N 17.8,
Found: C 58.1; H 7.82; N 17.6.

EXAMPLE 29

N-Phenyl-N'-[3-[3-(1-piperidinylmethyl)phenoxy]-propyl]1,3,4-oxadiazole-2,5-diamine 1.4 ml (10 mmol) of triethylamine and 0.7 ml (5 mmol) of phenyl isocyanide dichloride are added to 1.5 g (5 mmol) of N-[3-[3-(1-piperidinylmethyl)phenoxy]-propyl]-hydrazine carboxamide in 30 ml of THF and the mixture is stirred at room temperature until the reaction is quantitative. Solid triethylammonium chloride is filtered off, the filtrate is concentrated by evaporation under vacuum, and the solid residue is recrystallised from ethanol. The analytical values are summarized in Table II.

EXAMPLE 30

N-Benzyl-N'-[3-[3-(1-piperidinylmethyl)phenoxy]-propyl]1,3,4-oxadiazole-2,5-diamine The compound is prepared by a method analogous to that of Example 29 from N-[3-[3-(1-piperidinylmethyl) phenoxy]propyl]-hydrazine carboxamide and benzyl isocyanide dichloride. The analytical values are summarized in Table II.

EXAMPLE 31

N-Cyclohexyl-N'-[3-[3-(1-piperidinylmethyl)phenoxy]-propyl]-1,3,4-oxadiazole-2,5-diamine The compound is prepared by a method analogous to that of Example 29 from N-[3-[3-(1-piperidinylmethyl) phenoxy]propyl]-hydrazine carboxamide and cyclohexyl isocyanide dichloride. The analytical values are summarized in Table II.

EXAMPLE 32

N-Phenyl-N'-[3-[3-(1-piperidinylmethyl)phenoxy]-propyl]1,3,4-thiadiazole-2,5-diamine The compound is prepared by a method analogous to that of Example 29 from N-[3-[3-(1-piperidinylmethyl) phenoxy]propyl]-hydrazine carbothioamide and phenyl isocyanide dichloride. The analytical values are summarized in Table II.

EXAMPLE 33

N-Benzyl-N'-[3-[3-(1-piperidinylmethyl)phenoxy]-propyl]1,3,4-thiadiazole-2,5-diamine The compound is prepared by a method analogous to that of Example 29 from N-[3-[3-(1-piperidinylmethyl) phenoxy]propyl]-hydrazine carbothioamide and benzyl isocyanide dichloride. The analytical values are summarized in Table II.

TABLE II

Characteristics of the compounds of Examples 29 to 33 corresponding to the general formula

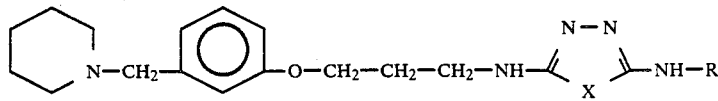

| Example | X R | Overall formula Molecular weight | Analysis: Calculated/Found C | H | N | Melting point °C. | Yield % of theoretical |
|---|---|---|---|---|---|---|---|
| 29 | O  C$_6$H$_5$ | C$_{23}$H$_{29}$N$_5$O$_2$  407.5 | 67.8  67.6 | 7.17  6.90 | 17.2  16.9 | 144 Decomposition  EtOH | 69 |
| 30 | O  CH$_2$C$_6$H$_5$ | C$_{24}$H$_{31}$N$_5$O$_2$  421.5 | 68.4  68.3 | 7.41  7.44 | 16.6  16.7 | 131–2  EtOH | 50 |
| 31 | O  c-C$_6$H$_{11}$ | C$_{23}$H$_{35}$N$_5$O$_2$  × HCl 450.0 | 61.4  61.4 | 8.06  8.16 | 15.6  15.8 | 208 decomposition  MeOH | 67 |
| 32 | S  C$_6$H$_5$ | C$_{23}$H$_{29}$N$_5$OS  423.6 | 65.2  65.2 | 6.90  6.94 | 16.5  16.5 | 141–3  EtOH | 75 |
| 33 | S  CH$_2$C$_6$H$_5$ | C$_{24}$H$_{31}$N$_5$OS  437.6 | 65.9  66.0 | 7.14  7.22 | 16.0  16.4 | 87–8  ACN | 42 |

EXAMPLE 34

N-[2-Methyl-3-[3-(1-piperidinylmethyl)phenoxy]-propyl]N'-phenyl-1,3,4-oxadiazole-2,5-diamine 0.96 g (3 mmol) of N-[2-methyl-3-[3-(1-piperidinyl-methyl)phenoxy]propyl]-hydrazine carboxamide are reacted and isolated by a method analogous to that of Example 29.

Yield: 0.61 g (48% of theoretical): melting point: 116° C. (acetonitrile)

C$_{24}$H$_{31}$N$_5$O$_2$ (421.5)

Calculated: C 68.4; H 7.41; N 16.6;

Found: C 68.0; H 7.22; N 16.6.

EXAMPLE 35

N-[2-Hydroxy-3-[3-(1-piperidinylmethyl)phenoxy]-propyl]- N'-phenyl-1,3,4-thiadiazole-2,5-diamine 0.68 g (2 mmol) of N-[2-hydroxy-3-[3-(1-piperidinyl-methyl)phenoxy]propyl]-hydrazine carbothioamide are reacted and isolated by a method analogous to that of Example 29.

Yield: 0.48 g (55% of theoretical); melting point 150°–152° C. (acetonitrile)

C$_{23}$H$_{29}$N$_5$O$_2$S (439.6;)

Calculated: C 62.8; H 6.65; N 15.9;

Found: C 62.7; H 6.57; N 16.1.

EXAMPLE 36

N-Methyl-N'-[3-[3-(1-piperidinylmethyl)phenoxy]-propyl]1,3,4-thiadiazole-2,5-diamine 2 ml of 30% Hydrogen peroxide are added to 1.58 g (4 mmol) of N-methyl-N'-[3-[3-(1-piperidinylmethyl)-phenoxy]propyl]-1,2-hydrazine dicarbothioamide in 30 ml of ethanol and the reaction mixture is briefly heated to boiling. The sulphur which separates is filtered off hot with the aid of active charcoal and the filtrate is concentrated by evaporation and purified by preparative layer chromatography.

Yield: 0.8 g of colourless foam (55% of theoretical) $C_{18}H_{27}N_5OS$ (361.5)

1H-NMR (DMSO-d6, TMS): $\delta = 1.1-1.7$ (m) (—$(CH_2)_3$—) 6H: 1.98 (m) (—$CH_2$—) 2H; 2.1-2.4 (m) (—$(CH_2)_2$—) 4H; 2.74 (d) (N-$CH_3$) 3H; 3.1-3.6 (m) (N—$CH_2$—) 2H; 3.35 (s) (N—$CH_2$—) 2H: 3.98 (t) (O—$CH_2$—) 2H; 6.5-7.4 (m) (aromatic-H, $(NH)_2$ (replaceable by $D_2O$)) 6H.

EXAMPLE 37

N-Ethyl-N'-[3-]3-(1-piperidinylmethyl)phenoxy]-propyl]1,3,4-thiadiazole-2,5-diamine 1.64 g (4 mmol) of N-ethyl-N'-[3-[3-(1-piperidinylmethyl)phenoxy]propyl]-1,2-hydrazine dicarbothioamide in 30 ml of ethanol are reacted and isolated in a manner analogous to Example 36.

Yield: 1.1 g of colourless foam (73% of theoretical): Melting point 102°-104° C.

$C_{19}H_{29}N_5OS$ (375.5)

Calculated: C 60.8; H 7.78; N 18.6;
Found: C 60.6; H 7.87; N 18.4.

1H-NMR (DMSO-d6, TMS): $\delta = 1.13$ (t) (C-$CH_3$) 3H; 1.1-1.7 (m)(—$(CH_2)_3$—) 6H: 1.98 (m) (—$CH_2$—) 2H; 2.1-2.4 (m) (—$(CH_2)_2$—) 4H; 2.9-3.6 (m) (N—$CH_2$—)_2) 4H; 3.35 (s) (N—$CH_2$—) 2H; 3.98 (t) (O—$CH_2$—) 2H; 6.5-7.4 (m) (aromatic-H, (2NH) (replaceable by $D_2O$)) 6 H.

Analogous reaction of N-cyclohexyl-N'-[3-[3-(1-piperidinylmethyl)-phenoxy]-propyl]-1,2-hydrazine dicarbothioamide yields a compound which is identical to that described hereinafter in Example 42.

EXAMPLE 38

N-Benzoyl-N'-[3-[3-(1-piperidinylmethyl)phenoxy]-propyl]1,3,4-thiadiazole-2,5-diamine 2.61 g (5 mmol) of N-benzoyl-N'-[3-[3-(1-piperidinylmethyl)phenoxy]propyl]-1,2-hydrazine dicarbothioamide hydrochloride are dissolved in 50 ml of ethanol with heating, and 2 ml of 30% hydrogen peroxide are added. The solution is briefly boiled up and the sulphur which separates if filtered off and the product is precipitated with ammonia solution and recrystallised from ethanol/water.

Yield: 1.65 g (73% of theoretical); melting point: 184°-186° C. (ethanol)

$C_{24}H_{29}N_5O_2S$ (451.6)

Calculated: C 63.8; H 6.47; N 15.5;
Found: C 63.8; H 6.45; N 15.4.

EXAMPLE 39

N-Benzoyl-N'-[2-hydroxy-3-[3-(1-piperidinylmethyl)-phenoxy]propyl]-1,3,4-thiadiazole-2,5-diamine 0.33 g (2 mmol) of benzoyl isothiocyanate are added to 0.68 g (2 mmol) of N-[2-hydroxy-3-[3-(1-piperidinylmethyl)phenoxy]propyl]-hydrazine carbothioamide in 20 ml of THF and the reaction mixture is stirred overnight at room temperature. After removal of the THF by evaporation, the solid residue is washed with ether and dissolved in 30 ml of ethanol with heating, and 1 ml of 30% hydrogen peroxide is added. The sulphur which separates is filtered off, the filtrate is concentrated by evaporation and the oily residue is purified by preparative layer chromotography.

Yield: 0.18 g of colourless foam (19% of theoretical) $C_{24}H_{29}N_5O_3S$ (467.6)

EXAMPLE 40

N-(1-Methylethyl)-N'-[3-[3-(1-piperidinylmethyl)-phenoxy]propyl]-1,3,4-thiadiazole-2,5-diamine 1.63 g (4 mmol) of N-(1-methylethyl)-2-[[3-[3-(1piperidinylmethyl)phenoxy]propyl]-aminothioxomethyl]hydrazine carboxamide in 10 ml of phosphorus oxychloride are stirred under slight reflux for one hour. The reaction mixture is then poured on 300 ml of ice water and adjusted to a pH of about 9 with concentrated ammonia solution. The resulting precipitate is separated off, washed with water and recrystallised from acetonitrile. The analytical values are summarised in Table III.

EXAMPLE 41

N-Butyl-N'-[3-[3-(1-piperidinylmethyl)phenoxy]-propyl]1,3,4-thiadiazole-2,5-diamine The compound is prepared by a method analogous to that of Example 40 from N-butyl-2-[[3-[3-(1-piperidinylmethyl)phenoxy]propyl]aminothioxomethyl]hydrazine carboxamide and phosphorus oxychloride. The analytical values are summarized in Table III.

EXAMPLE 42

N-Cyclohexyl-N'-[3-[3-(1-piperidinylmethyl)phenoxy]-propyl]1,3,4-thiadiazole-2,5-diamine The compound is prepared by a method analogous to that of Example 40 from N-cyclohexyl-2-[[3-[3-(1-piperidinylmethyl)phenoxy]propyl]aminothioxomethyl]-hydrazine carboxamide and phosphorus oxychloride. The analytical values are summarized in Table III.

EXAMPLE 43

N-4-Chlorophenyl-N'-[3-[3-(1-piperidinylmethyl)-phenoxy]propyl]-1,3,4-thiadiazole-2,5-diamine The compound is prepared by a method analogous to that of Example 40 from N-4-chlorophenyl-N'-[[3-[3-(1piperidinylmethyl)phenoxy]propyl]aminothioxomethyl]hydrazine carboxamide and phosphorus oxychloride. The analytical values are summarized in Table III.

EXAMPLE 44

N-Methyl-N'-[3-[3-(1-piperidinylmethyl)phenoxy]-propyl]1,3,4-oxadiazole-2,5-diamine The compound is prepared by a method analogous to that of Example 40 from N-methyl-N'-[3-[3-(1-piperidinylmethyl)phenoxy]propyl]-1,2-hydrazine dicarboxamide and phosphorus oxychloride. The analytical values are summarized in Table III.

EXAMPLE 45

N-Ethyl-N'-[3-[3-(1-piperidinylmethyl)phenoxy]-propyl]1,3,4-oxadiazole-2,5-diamine The compound is prepared by a method analogous to that of Example 40 from N-ethyl-N'-[3-[3-(1-piperidinylmethyl)phenoxy]propyl]-1,2-hydrazine dicarboxamide and phosphorus oxychloride. The analytical values are summarized in Table III.

EXAMPLE 46

N-Isopropyl-N'-[3-[3-(1-piperidinylmethyl)phenoxy]-propyl]1,3,4-oxadiazole-2,5-diamine The compound is prepared by a method analogous to that of Example 40 from N-isopropyl-N'-[3-[3-(1-piperidinylmethyl)phenoxy]propyl]-1,2-hydrazine dicarboxamide and phosphorus oxychloride. The analytical values are summarized in Table III.

EXAMPLE 47

N-4-Chlorophenyl-N'-[3-[3-(1-piperidinylmethyl)-phenoxy]propyl]-1,3,4-oxadiazole-2,5-diamine The compound is prepared by a method analogous to that of Example 40 from N-4-chlorophenyl-N'-[3-[3-(1piperidinylmethyl)phenoxy]propyl]-1,2-hydrazine dicarboxamide and phosphorus oxychloride. The analytical values are summarized in Table III.

EXAMPLE 49

N,N-Dimethyl-N'-[3-[3-(1-piperidinylmethyl)phenoxy]-propyl]1,3,4-oxadiazole-2,5-diamine 1.13 g (3 mmol) of N,N-dimethyl-N'-[3-[3-(1-piperidinylmethyl)phenox]propyl]-1,2-hydrazine dicarboxamide are reacted and isolated in a manner analogous to Example 40.

Yield: 0.65 g (60% of theoretical); melting point:132° C. decomposition (acetonitrile)

$C_{19}H_{29}N_5O_2$ (359.5)

Calculated: C 63.5; H 8.13; N 19.5;
Found: C 63.3; H 8.10; N 19.4.

EXAMPLE 50

N-[3-[3-(1-Piperidinylmethyl)phenoxy]propyl]-1,3,4-thiadiazole-2,5-diamine 0.9 g (2 mmol) of N-benzoyl-N'-[3-[3-(1-piperidinyl-

TABLE III

Characteristic data of the compounds according to the invention of Examples 40 to 47 corresponding to the general formula

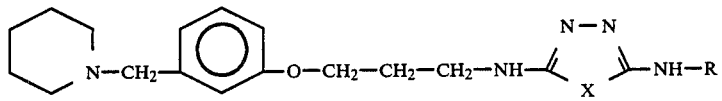

| Example | X<br>R | Overall formula<br>Molecular weight | Analysis:<br>Calculated/Found | | | Melting<br>point °C. | Yield % of<br>theoretical |
|---|---|---|---|---|---|---|---|
| | | | C | H | N | | |
| 40 | S<br>$CH(CH_3)_2$ | $C_{20}H_{31}N_5OS$<br>389.6 | 61.7<br>61.7 | 8.02<br>8.08 | 18.0<br>18.3 | 110-1 | 67 |
| 41 | S<br>$C_4H_9$ | $C_{21}H_{33}N_5OS$<br>403.6 | 62.5<br>62.5 | 8.24<br>8.16 | 17.4<br>17.3 | 98-100 | 70 |
| 42 | S<br>$c\text{-}C_6H_{11}$ | $C_{23}H_{35}N_5OS$<br>429.6 | 64.3<br>64.1 | 8.21<br>8.26 | 16.3<br>16.3 | 130-2 | 68 |
| 43 | S<br>$4\text{-}Cl\text{-}C_6H_4$ | $C_{23}H_{28}ClN_5OS$<br>458.0 | 60.3<br>60.4 | 6.16<br>6.21 | 15.3<br>15.3 | 174-6 | 52 |
| 44 | O<br>$CH_3$ | $C_{18}H_{27}N_5O_2$<br>× 0,5 $H_2O$<br>354.5 | 61.0<br>61.0 | 7.96<br>8.00 | 19.8<br>19.5 | 152<br>Decomposition | 60 |
| 45 | O<br>$C_2H_5$ | $C_{19}H_{29}N_5O_2$<br>× 0.5 $H_2O$<br>368.5 | 61.9<br>62.2 | 8.21<br>7.89 | 19.0<br>19.0 | 129 | 64 |
| 46 | O<br>$CH(CH_3)_2$ | $C_{20}H_{31}N_5O_2$<br>× HCl × 0.5<br>$H_2O$<br>419.0 | 57.3<br>57.3 | 7.94<br>7.69 | 16.7<br>16.9 | 184<br>Decomposition | 54 |
| 47 | O<br>$4\text{-}Cl\text{-}C_6H_4$ | $C_{23}H_{28}ClN_5O_2$<br>× HCl × 0.5<br>$H_2O$<br>487.4 | 56.7<br>56.5 | 6.20<br>6.12 | 14.4<br>14.0 | 183<br>Decomposition | 56 |

EXAMPLE 48

N,N-Dimethyl-N'-[3-[3-(1-piperidinylmethyl)phenoxy]-propyl]1,3,4-thiadiazole-2,5-diamine 1.18 g (3 mmol) of N,N-dimethyl-2-[[3-[3-(1-piperidinylmethyl)phenoxy]propyl]-aminothioxomethyl]hydrazine carboxamide are reacted and isolated in a manner analogous to Example 40.

Yield: 0.8 g (71% of theoretical): melting point: 128°-129° C. (ethanol/water)

$C_{19}H_{29}N_5OS$ (375.5)

Calculated: C 60.8; H 7.78; N 18.6;
Found: C 60.5; H 7.76; N 18.8.

methyl)phenoxy]propyl]-1,3,4-thiadiazole-2,5-diamine are heated under reflux in 20 ml of concentrated hydrochloric acid for 2 hours. After evaporation of the hydrochloric acid to dryness, the solid residue is first digested with ether and then dissolved in a small quantity of ethanol, and the product is precipitated with concentrated ammonia solution and recrystallised from ethanol/water.

Yield: 0.5 g (70% of theoretical); melting point: 158°-159° C. (ethanol/water).

$C_{17}H_{25}N_5OS$ (347.5)

Calculated: C 58.8; H 7.25; N 20.2;
Found: C 58.8; H 7.28; N 20.0.

EXAMPLE 51

N-[4-[3-(1-piperidinylmethyl)phenoxy]-2-butenyl]-1,3,4-thiadiazole-2,5-diamine 0.6 g (2.3 mmol) of 4-[3-(1-piperidinylmethyl)phenoxy]2-butene-1-amine, 0.35 ml of triethylamine and 0.42 g (2.3 mmol) of 5-bromo-1,3,4-thiadiazole-2-amin are heated under reflux in 20 ml of THF for 3 hours. Solid triethylammonium bromide is filtered off, the filtrate is concentrated by evaporation and the oily residue is purified by preparative layer chromatography.

Yield: 0.25 g (30% of theoretical); melting point 131°–134° C.

$C_{18}H_{25}N_5OS$ (359.4)

Calculated: C 60.1; H 7.01; N 19.5;
Found: C 60.2; H 7.13; N 19.6.

1H-NMR (CDCl$_3$TMS): $\delta$=1.2–1.7 (m) (—(CH$_2$)$_3$—) 6H; 2.1–2.6 (m) (—(CH$_2$)$_2$—) 4H; 3.49 (s) (N—CH$_2$—) 2H; 3.6–4.0 (m) (N—CH$_2$—) 2H: 4.15–4.55 (m) (O—CH$_2$—) 2H; 5.83 (m) (CH=CH) 2H; 6.15 (broad s) (NH$_2$ (replaceable by D$_2$O)): 6.6–7.2 (m) (aromatic-H, (NH) (replaceable by D$_2$O )) 5H.

EXAMPLE 52

1-[(5-Amino-1,3,4-thiadiazol-2-yl)amino]-3-[3-(1-piperidinylmethyl)phenoxy]-2-propanol 0.54 g (3 mmol) of 5-bromo-1,3,4-thiadiazole-2-amine and 0.45 ml of triethylamine are added to 0.8 g (3 mmol) of 1-amino-3-[3-(1-piperidinylmethyl)phenoxy]-2-propanol in 20 ml of THF and the mixture is reacted in a manner analogous to Example 51. The oil obtained is purified by column chromatography (silica gel; ammoniacal. Methanolchloroform solution (5+95)).

Yield: 0.3 g (28% of theoretical); melting point 130°–132° C.

$C_{17}H_{25}N_5O_2S$ (363.5)

Calculated: C 56.2; H 6.93; N 19.3;
Found: C 55.7; H 6.96; N 19.5.

1H-NMR (d$_6$-DMSO,TMS) $\delta$=1.25–1.55 (m) (C-(CH$_2$)$_3$-C) 6H; 2.30 (m) (N(CH$_2$)$_2$) 4H: 3.32 (m) (CH$_2$—NH) 2H; 3.37 (s) (N-CH$_2$) 2H; 3.85–4.10 (m) (O—CH$_2$—CHOH) 3H; 5.27 (d) 1H; 6.24 (s) 2H; 6.78–6.90 (m) 4H; 7.21 (t) 1H ppm.

EXAMPLE 53

(±)-N-[2-methyl-3[3-(1-piperidinylmethyl)phenoxy]-propyl]-1,3,4-thiadiazole-2,5-diamine The compound is prepared by a method analogous to Example 51 from 2-methyl-3-[3-(1-piperidinylmethyl)phenoxy]-1-propanamine and 5-bromo-1,3,4-thiadiazole-2-amine.

Yield: 74% of theoretical; melting point: 133°–135° C.

$C_{18}H_{27}N_5OS$ (361.5)

Calculated: C 59.8; H 7.53; N 19.4;
Found: C 59.8; H 7.49; N 19.4.

1H-NMR (d$_6$-DMSO, TMS): $\delta$=1.01 (d) (CH$_3$) 3H; 1.25–1.55 (m) (C—CH$_2$)$_3$—C) 6H; 2.15–2.40 (m) (N(CH$_2$)$_2$, CH—CH$_3$) 5H; 3.20 (m) (CH$_2$—NH) 2 H; 3.37 (s) (N-CH$_2$) 2H; 3.85 (m) (O—CH$_2$) 2H; 6.23 (s) 2 H; 6.78–6.90 (m) 4H; 7.20 (t) 1H, ppm.

EXAMPLE 54

N-[3-[3-[(Dimethylamino)methyl]phenoxy]propyl]-1,3,4-thiadiazole-2,5-diamine

The compound is prepared by a method analogous to that of Example 51 from 3-[3-[(dimethylamino)methyl]phenoxy]-1-propanamine and 5-bromo-1,3,4-thiadiazole-2amine.

Yield: 38% of theoretical; melting point: 130°–131° C.

$C_{14}H_{21}N_5OS$ (307.4)

Calculated: C 54.7; H 6.89; N 22.8;
Found: C 54.7; H 6.80; N 22.9.

1H-NMR (d$_6$-DMSO, TMS): $\delta$=1.97 (quin.) (O—CH$_2$—CH$_2$) 2H; 2.13 (s) (N(CH$_3$)$_2$ 6H: 3.29 (q) (CH$_2$-NH) 2H; 3.34 (s) (N—CH$_2$) 2H: 4.01 (t) (O—CH$_2$) 2H; 6.24 (s) 2H; 6.80–6.90 (m) 4H; 7.22 (t) 1H ppm.

EXAMPLE 55

N-[3-[3-(1-Pyrrolidinylmethyl)phenoxy]propyl]-1,3,4-thiadiazole-2,5-diamine

The compound is prepared by a method analogous to that of Example 51 from 3-[3-(1-pyrrolidinylmethyl)phenoxy]1-propanamine and 5-bromo-1,3,4-thiadiazole-2-amine.

Yield: 66% of theoretical; melting point: 138°–140° C.

$C_{16}H_{23}N_5OS$ (333.5)

Calculated: C 57.6; H 6.95; N 21.0;
Found: C 57.6; H 6.75; N 21.0.

1H-NMR (d$_6$-DMSO TMS): $\delta$=1.69 (m) (C—(CH$_2$)$_2$—C) 4H; 1.97 (quin.) (O—CH$_2$—CH$_2$) 2H; 2.41 (m) (N(CH$_2$)$_2$ 4H: 3.29 (q) (CH$_2$—NH) 2H: 3.52 (s) (N—CH$_2$)2H; 4.01 (t) (O—CH$_2$) 2H; 6.24 (s) 2H: 6.75–6.90 (m) 4H; 7.21 (t) 1H ppm.

EXAMPLE 56

N-[3-[3-(1-Piperidinylmethyl)phenoxy]propyl]-1,3,4-thiadiazole-2,5-diamine

The compound is prepared by a method analogous to that of Example 51 from 3-[3-(1-piperidinylmethyl)phenoxy]-1-propanamine and 5-bromo-1,3,4-thiadiazole-2-amine. The product obtained is identical to the substance described in Example 50.

Yield: 55% of theoretical: melting point: 158°–159° C.

EXAMPLE 57

N-[3-[3-[(Hexahydro-1H-azepin-1-yl)methyl]phenoxy]-propyl]-1,3,4-thiadiazole-2,5-diamine The compound is prepared by a method analogous to that of Example 51 from 3-[3-[(hexahydro-1H-azepin-1-yl) methyl]phenoxy]-1-propanamine and 5-bromo-1,3,4-thiadiazole-2-amine.

Yield: 69% of theoretical: melting point: 140°–142° C.

$C_{18}H_{27}N_5OS$ (361.5)

Calculated: C 59.8; H 7.53; N 19.4;
Found: C 59.7; H 7.46; N 19.6.

1H-NMR (d$_6$-DMSO, TMS): $\delta$=1.56 (m) (C—CH$_2$)$_4$—C) 8H: 1.97 (quin.) (O—CH$_2$—CH$_2$) 2H; 2.55 (m) (N(CH$_2$)$_2$ 4H; 3.29 (q) (CH$_2$—NH) 2H; 3.55 (s) (N—CH$_2$) 2H; 4.01 (t) (O—CH$_2$) 2H; 6.24 (s) 2H; 6.75–6.90 (m) 4H; 7.21 (t) 1H ppm.

EXAMPLE 58

N-[3-[3-(4-Morpholinylmethyl)phenoxy]propyl]-1,3,4-thiadiazole-2.5-diamine

The compound is prepared by a method analogous to that of Example 51 from 3-[3-(4-morpholinylmethyl)phenoxy]1-propanamine and 5-bromo-1,3,4-thiadiazole-2-amine.

Yield: 60% of theoretical; melting point 170°–172° C.

$C_{16}H_{23}N_5O_2S$ (349.5)

Calculated: C 55.0; H 6.63; N 20.0;
Found: C 54.9; H 6.57; N 19.8.

1H-NMR (d$_6$-DMSO, TMS): δ=1.96 (quin.) (O—CH$_2$—CH$_2$) 2H; 2.33 (m) (N(CH$_2$)$_2$) 4H; 3.29 (q) (CH$_2$—NH) 2H; 3.41 (s) (N—CH$_2$) 2H; 3.57 (m) (O(CH$_2$)$_2$) 4H; 4.01 (t) (O—CH$_2$) 2H; 6.25 (s) 2H; 6.79–6.88 (m) 4H; 7.22 (t) 1H ppm.

EXAMPLE 59

N-[3-[3-[(4-Methyl-1-piperazinyl)methyl]phenoxy]-propyl]1,3,4-thiadiazole-2,5-diamine The compound is prepared by a method analogous to that of Example 51 from 3-[3-[(4-methyl-1-piperazinyl)methyl]phenoxy]-1-propanamine and 5-bromo-1,3,4-thiadiazole-2-amine.

Yield: 63% of theoretical; melting point: 146°–148° C. C$_{17}$H$_{26}$N$_6$OS (362.5)

Calculated: C 56.3; H 7.22; N 23.2;

Found: C 56.4; H 7.03; N 23.4.

1H-NMR (d$_6$-DMSO, TMS): δ=1.97 (quin.) (O—CH$_2$—CH$_2$) 2H; 2.14 (s) (N—CH$_3$) 3H; 2.20–2.40 (m) (piperazine) 8H; 3,29 (q) (CH$_2$—NH) 2H: 3.40 (s) (N—CH$_2$) 2H; 4.01 (t) (O—CH$_2$) 2H; 6.24 (s) 2H; 6.78–6.87 (m) 4H; 7.21 (t) 1H ppm.

EXAMPLE 60

N-[3-[3-(1-Piperidinylmethyl)phenoxy]propyl]-1,3,4-oxadiazole-2,5-diamine

The compound is prepared by a method analogous to that of Example 40 from N-[3-[3-(1-piperidinylmethyl)phenoxy]propyl]-1,2-hydrazine dicarboxamide and phosphorus oxychloride.

Yield: 25% of theoretical: melting point: 114° C. C$_{17}$H$_{25}$N$_5$O$_2$ (331.4)

Calculated: C 61.6; H 7.60; N 21.1;

Found: C 61.4; H 7.87; N 20.9.

1H-NMR (d$_6$-DMSO, TMS): δ=1.25–1.55 (m) (C-CH$_2$)$_3$-C) 6H; 1.96 (quin.) (O—CH$_2$—CH$_2$) 2H; 2.30 (m) (N—CH$_2$)$_2$) 4H; 3.21 (q) (CH$_2$—NH) 2H; 3.37 (s) (N—CH$_2$) 2H: 4.00 (t) (O—CH$_2$) 2H; 6.29 (s) 2H: 6.75–6.90 (m) 4H; 7.21 (t) 1H ppm.

EXAMPLE 61

(±)-N-[2-Methyl-3-[3-(1-piperidinylmethyl)phenoxy]-propyl]1,3,4-oxadiazole-2,5-diamine 7 mmol of N-[2-Methyl-3-[3-(1-piperidinylmethyl)phenoxy]propyl]-1,2-hydrazine dicarboxamide in 30 ml of phosphorus oxychloride are stirred for 6 hours at 50°–60° C. When cooled, the reaction mixture is poured out on 300 ml of ice water and neutralized by the addition of concentrated ammonia solution with cooling. The product is extracted with ether and the combined ether extracts are washed, dehydrated and concentrated by evaporation. The solid residue is recrystallised from ether.

Yield: 20% of theoretical: melting point: 92° C. C$_{18}$H$_{27}$N$_5$O$_2$ (345.5)

Calculated: C 62.6; H 7.88; N 20.3;

Found: C 62.5; H 7.72; N 20.2.

1H-NMR (CDCl$_3$, TMS): δ=1.08 (d) (CH$_3$) 3H; 1.25–1.55 (m) (C—(CH$_2$)$_3$—C) 6H; 2.10–2.50 (m) (N(CH$_2$)$_2$,CH—CH$_3$) 5H; 3.15–3.50 (m) (CH$_2$—NH, N—CH$_2$) 4H; 3.65–4.00 (m) (O—CH$_2$) 2H; 4.50–5.20 (3H); 6.60–7.30 (m) 4H ppm.

EXAMPLE 62

N-[3-[3-(4-Thiomorpholinylmethyl)phenoxy]propyl]-1,3,4-thiadiazole-2,5-diamine diazole-2,5-diamine The compound is prepared by a method analogous to that of Example 51 from 3-[3-(4-thiomorpholinylmethyl)phenoxy]-1-propanamine and 5-bromo-1,3,4-thiadiazole-2-amine.

Yield: 58% of theoretical; melting point 158°–160° C. C$_{16}$H$_{23}$N$_5$OS (365.5)

Calculated: C 52.6; H 6.34; N 19.2;

Found: C 52.5; H 6.32; N 19.4.

1H-NMR (d$_6$-DMSO, TMS): δ=1.97 (quin.) (CH$_2$) 2H: 2.60 (s) (—(CH$_2$)$_4$—) 8H; 3.29 (q) (CH$_2$) 2H; 3.45 (s) (CH$_2$) 2H; 4.01 (t) (CH$_2$) 2H; 6.25 (s) 2H; 6.80–6.89 (m) 4H; 7.22 (t) 1H ppm.

EXAMPLE 63

N-[4-[3-(1-Piperidinylmethyl)phenoxy]butyl]-1,3,4-thiadiazole-2,5-diamine

The compound is prepared by a method analogous to that of Example 51 from 4-[3-(1-piperidinylmethyl)-phenoxy]1-butanamine and 5-bromo-1,3,4-thiadiazole-2-amine.

Yield: 61% of theoretical: melting point: 139° C. C$_{18}$H$_{27}$N$_5$OS (361.5)

Calculated: C 59.8; H 7.53; N 19.4;

Found: C 59.9; H 7.45; N 19.5.

1H-NMR (d$_6$-DMSO, TMS): δ=1.20–1.67 (m) (—(CH$_2$)$_3$—) 6H; 1.73 (m) (—(CH$_2$)$_2$—) 4H; 2.33 (m) (—(CH$_2$)$_2$—) 4 H; 3.20 (m) (—CH$_2$—, N—H) 3H; 3.40 (s) (—CH$_2$—) 2H; 4.00 (t) (—O—CH$_2$—) 2H: 6.17 (s) (—NH$_2$) 2H; 6.67–7.40 (m) 4H ppm.

EXAMPLE 64

N-[3-[3 (3-Methylpiperidin-1-yl-methyl)phenoxy]propyl]1,3,4-thiadiazole-2,5-diamine Preparation of the preliminary stages (a) 3-[(3-Methylpiperidin-1-yl)methyl]phenol 24.4 g (0.2 mol) of 3-hydroxybenzaldehyde are mixed with 40 ml (about 0.4 mol) of 3-methylpiperidine and 20 ml (about 0.52 mol) of 100% formic acid with cooling and then stirred for 2 hours at 120° C. When the reaction mixture has cooled to room temperature, it is poured into water and rendered alkaline with ammonia, and the precipitated solid is filtered off and recrystallised from ethanol.

Yield: 37 g (90% of theoretical): melting point: 155°–157° C.

(b) 3-[3-[(3-Methylpiperidin-1-yl)methyl]phenoxy]-propanamine 5.13 g (0.025 mol) of 3-[(3-Methylpiperidin-1-yl) methyl]phenol are introduced into a suspension of 1.0 g (0.025 mol) of sodium hydride (60%) in absolute DMF and stirred overnight at room temperature. After the addition of 2.23 g (0.025 mol) of 3-chloropropionic acid nitrile, the reaction mixture is stirred for 7 hours at 60° C. and then poured into ice water and extracted with ether, and the organic phase is washed with 5% NaOH. After dehydration over Na$_2$SO$_4$, the ethereal phase is introduced dropwise into a suspension of 1.14 g (0.03 mol) of LiAlH$_4$ in absolute ether and then hydrolysed with 2.2 ml of H$_2$O. After filtration and removal of solvent by evaporation under vacuum, 2.96 g of a pale yellow oil are left behind.

N-3-[3-(3-Methylpiperidin-1-yl-methyl)phenoxy]-
propyl]1,3,4-thiadiazole-2,5-diamine The compound is prepared by a method analogous to that of Example 51 from 3-[3-[(3-methylpiperidin-1-yl) methyl]phenoxy]propanamine and 5-bromo-1,3,4-thiadiazole-2-amine.

Yield: 45% of theoretical: melting point: 138.5°–140.0° C.

$C_{18}H_{27}N_5OS$ (361.5)

Calculated: C 59.8; H 7.48; N 19.39;

Found: C 59.7; H 7.45; N 19.11.

1H-NMR ($d_6$-DMSO, TMS): $\delta$=0.8 (d) 3H; 1.28–2.16 (m) 9H; 2.58–2.8 (m) 2H; 3.27 (t) 2H; 3.4 (s) 2H: 4.03 (t) 2H; 6.27 (s) 2H; 6.7–7.37 (m) 5H ppm.

EXAMPLE 65

N-[4-[3-(3-Methylpiperidin-1-yl-methyl)phenoxy]-butyl]1,3,4-thiadiazole-2,5-diamine Preparation of the preliminary stage (a)  4-[3-[(3-Methylpiperidin-1-yl)methyl]phenoxy]-butanamine 5.13 g (0.025 mol) of 3-((methylpiperidin-1-yl)methyl) phenol (Example 64 a) are added to a suspension of 1.0 g (0.025 mol) of sodium hydride (60%) in absolute DMF and the mixture is stirred overnight at room temperature. After the addition of 2.58 g (0.025 mol) of 4chlorobutyronitrile, the reaction mixture is stirred at 60° C. for 7 hours, and then poured into ice water and extracted with ether, and the organic phase is washed with 5% NaOH. After dehydration over $Na_2SO_4$, the ethereal phase is introduced dropwise into a suspension of 1.14 g (0.03 mol) of $LiAlH_4$ in absolute ether and then hydrolysed with 2.2 ml $H_2O$. After removal of the inorganic constituents by filtration and evaporation of the solvent under vacuum, 3.66 g of a pale yellow oil are left behind.

N-[4 [3-((3-Methylpiperidin-1-yl)methyl)phenoxy]-butyl]1,3,4-thiadiazole-2,5-diamine.

The compound is prepared by a method analogous to that of Example 51 from 4-[3-[(3-methylpiperidin-1-yl) methyl]phenoxy]-butanamine and 5-bromo-1,3,4-thiadiazole2-amine. Yield: 54% of theoretical: melting point: 123°–124° C.

$C_{19}H_{29}N_5OS$ (375.5)

Calculated: C 60.8; H 7.78; N 18.6;

Found: C 60.8; H 7.78; N 18.7.

1H-NMR ($CDCl_3$; TMS) $\delta$=0.82–0.96 (m) 4H; 1.52–1.76 (m) 5H; 1.82–1.94 (m) 5H; 2.52 (m) 2H; 3.36 (dt) 2H; 3.46 (s) 2H; 4.0 (t) 2H; 5.02 (s) 2H; 5.42 (s) 1H; 6.8 (m) 1H; 6.92 (m) 2H; 7.22 (m) 1H ppm.

EXAMPLE 66

N-[3-[3-((3-Methylpyrrolidin-1-yl)methyl)phenoxy]-propyl]1,3,4-thiadiazole-2,5-diamine Preparation of the preliminary stages (a) 3-[(3-Methylpyrrolidin-1-yl)methyl]phenol This compound is prepared by a method analogous to that of Example 64 a from 3-methyl-pyrrolidine.

Yield: 85% of theoretical (yellow oil)

(b) 3-[3-[(3-Methylpyrrolidin-1-yl)-methyl]phenoxy]-propanamine 28.7 g (0.15 mol) of 3-[(3-methylpyrrolidin-1-yl) methyl]phenol are heated under reflux together with 100 ml of acrylonitrile and 1.5 ml of 40% methanolic benzyltrimethylammonium hydroxide solution for 18 hours. The excess acrylonitrile is evaporated off under vacuum and the residue is taken up with ether, washed with 5% NaOH and reduced to the amine by reaction with 7.6 g (0.2 mol) of $LiAlH_4$ in a manner analogous to Example 64 b. 14.9 g (40% of theoretical) of a pale yellow oil is obtained in a sufficiently pure form for subsequent reactions.

N-[3-[3-((3-Methylpyrrolidin-1-yl)methyl)phenoxy]-propyl]1,3,4-thiadiazole-2,5-diamine The compound is prepared by a method analogous to that of Example 51 from 3-[3-[(3-methylpyrrolidin-1-yl) methyl]phenoxy]propanamine and 5-bromo-1,3,4-thiadiazole-2-amine.

Yield: 48% of theoretical: melting point: 116°–119° C.

$C_{17}H_{25}N_5OS$ (347.5)

Calculated: C 58.8; H 7.25; N 20.2;

Found: C 58.7; H 7.24; N 20.1.

1H-NMR ($CDCl_3$, TMS): $\delta$=1.0 (d) 3H; 1.24 (m) 1H; 1.96–2.34 (m) 5H: 2.46 (m) 1H; 2.74 (m) 1H; 2.84 (m) 1H; 3.5 (dt) 2H; 3.56 (s) 2H; 4.08 (t) 2H: 4.8 (s) 2H; 5.36 (s) 1H; 6.79 (m) 1H; 6.91 (m) 2H; 7.21 (m) 1H ppm.

EXAMPLE 67

N-[4-[3-((3-Methylpyrrolidin-1-yl)methyl)phenoxy]-butyl]1,3,4-thiadiazole-2,5-diamine Preparation of the preliminary stage (a)  4-[3-[(3-Methylpyrrolidin-1-yl)methyl]phenoxy]-butanamine The compound is prepared by a method analogous to that of Example 65 a from 3-[(3-methylpyrrolidin-1-yl) methyl]phenol. A pale yellow oil sufficiently pure for subsequent reactions is obtained.

Yield: 60% of theoretical N-[4-[3-((3-Methylpyrrolidin-1-yl)methyl)phenoxy]butyl]1,3,4-thiadiazole-2,5-diamine The compound is prepared by a method analogous to that of Example 51 from 4-[3-[(3-methylpyrrolidin-1-yl) methyl]-phenoxy]-butanamine and 5-bromo-1,3,4-thiadiazole-2-amine.

Yield: 50% of theoretical; melting point: 118°–119° C.

$C_{18}H_{27}N_5OS$ (361.5)

Calculated: C 59.8; H 7.52; N 19.4;

Found: C 59.8; H 7.66; N 19.3.

1H-NMR ($CDCl_3$), TMS): $\delta$=1.0 (d) 3H; 1.26–1.4 (m) 1H; 1.78–1.92 (m) 4H; 1.94–2.1 (m) 2H; 2.18–2.34 (m) 1H: 2.38–2.5 (m) 1H; 2.68–2.78 (m) 1H; 2.8–2.88 (m) 1H; 3.36 (dt) 2H; 3.58 (s) 2H; 4.0 (t) 2H; 4.9 (s) 2H; 5.28 (s) 1H; 6.78 (m) 1H; 6.9 (m) 2H; 7.22 (m) 1H ppm.

EXAMPLE 68

N-[3-[3-[(2,6-Dimethyl-1-piperidinyl)methyl]phenoxy]-propyl]1,3,4-thiadiazole-2,5-diamine The compound is prepared by a method analogous to that of Example 51 from 3-[3-[(2,6-dimethyl-1-piperidinyl) methyl]phenoxy]-1-propanamine and 5-bromo-1,3,4-thiadiazole-2-amine.

Yield 43% of theoretical; melting point: 149°–151° C.

$C_{19}H_{29}N_5OS$ (375.5)

Calculated: C 60.8; H 7.78; N 18.6;

Found: C 60.7; H 7.64; N 18.7.

1H-NMR ($d_6$-DMSO, TMS): $\delta$=0.94 (d) ($CH_3$) 6H: 1.15–1.65 (m) (($CH_2$)$_3$) 6H; 1.97 (quin) ($CH_2$) 2H; 2.43 (m) (N($CH_2$)$_2$ 2H; 3.29 (q) ($CH_2$) 2H; 3.66 (s) (N—$CH_2$) 2H; 4.00 (t) ($CH_2$) 2H; 6.24 (s) 2H: 6.73–6.95 (m) 4H; 7.18 (t) 1H ppm.

EXAMPLE 69

N-[3-[3-[(3,5-Dimethyl-1-piperidinyl)methyl]phenoxy]-propyl]-1,3,4-thiadiazole-2,5-diamine The compound is prepared by a method analogous to that of Example 51 from 3-[3-[(3,5-dimethyl-1-piperidinyl) methyl]phenoxy]-1-propanamine and 5-bromo-1,3,4-thiadiazole-2-amine.

Yield 46% of theoretical; melting point 112°–116° C. $C_{19}H_{29}N_5OS$ (375.5)

Calculated: C 60.8; H 7.78; N 18.6;

Found: C 60.7; H 7.77; N 18.6.

1H-NMR (CDCl$_3$, TMS): δ=0.50–2.90 (m) 16H; 3.45 (s) (N—CH$_2$) 2H; 3.51 (t) (CH$_2$—NH) 2H; 4.08 (t) (O—CH$_2$) 2H; 4.60–4.90 2H; 5.10–5.40 1H; 6.74–6.93 (m) 3H; 7.22 (t) 1H ppm.

EXAMPLE 70

N-[3-[3-[(4-Methyl-1-piperidinyl)methyl]phenoxy]-propyl]1,3,4-thiadiazole-2,5-diamine The compound is prepared by a method analogous to that of Example 51 from 3-[3-[(4-methyl-1-piperidinyl)-methyl]phenoxy]-1-propanamine and 5-bromo-1,3,4-thiadiazole-2-amine.

Yield: 64% of theoretical: melting point: 141°–143° C. $C_{18}H_{27}N_5OS$ (361.5)

Calculated: C 59.8; H 7.53; N 19.4;

Found: C 59.8; H 7.29; N 19.3.

1H-NMR (CDCl$_3$, TMS): δ=0.91 (d) (CH$_3$) 3H; 1.15–2.00 (m) 7H; 2.12 (quin.) (O—CH$_2$—CH$_2$) 2H: 2.84 (m) 2H; 3.45 (s) (N—CH$_2$) 2H: 3.51 (t) (CH$_2$—NH) 2H; 4.08 (t) (O—CH$_2$) 2H; 4.60–4.80 2H: 5.10–5.40 1H; 6.75–6.92 (m) 3H: 7.21 (t) 1H ppm.

What is claimed is:

1. 1,3,4-Thiadiazole derivatives corresponding to the formula

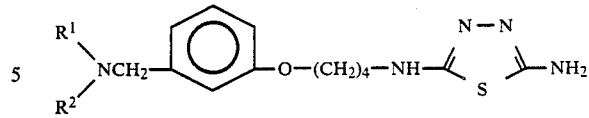

wherein $R^1$ and $R^2$ together with the nitrogen atom to which they are attached represent a piperidine ring optionally substituted with a methyl group; and their physiologically acceptable acid addition salts.

2. The compound of claim 1 wherein $R^1$ and $R^2$ together with the nitrogen atom to which they are attached represent a piperidin-1-yl group.

3. The compound of claim 1 wherein $R^1$ and $R^2$ together with the nitrogen atom to which they are attached represent a 3-methylpiperidin-1-yl group.

4. 1,3,4-Thiadiazole derivatives corresponding to the formula

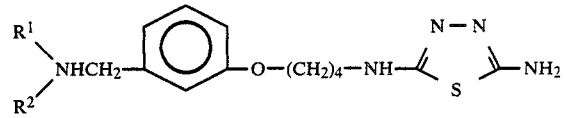

wherein $R^1$ and $R^2$ taken together with the nitrogen atom to which they are attached represent a pyrrolidine ring optionally substituted with a methyl group; and their physiologically acceptable acid addition salts.

5. The compound of claim 4 wherein said compound is N-[4-[3-((3-methylpyrrolidin-1-yl)methyl)phenoxy]-butyl]-1,3,4-thiadiazole-2,5-diamine and its physiologically acceptable salts.

6. An anti-ulcer formulation comprising a compound of claim 1, claim 2, claim 3, claim 4, or claim 5 in an amount effective to inhibit histamine-H$_2$ receptors, in combination with a pharmaceutically acceptable carrier or diluent therefor.

* * * * *